United States Patent [19]

Murata et al.

[11] 4,433,320
[45] Feb. 21, 1984

[54] DEW SENSOR

[75] Inventors: Michihiro Murata, Kyoto; Akira Kumada, Ootsu, both of Japan

[73] Assignee: Murata Manufacturing Co., Ltd., Japan

[21] Appl. No.: 409,028

[22] Filed: Aug. 18, 1982

[51] Int. Cl.³ .............................................. H01L 7/00
[52] U.S. Cl. ..................................... 338/35; 338/308; 338/320
[58] Field of Search ................... 338/34, 35, 309, 319, 338/320, 308; 73/336.5, 338, 335; 422/98; 340/602; 200/61.06; 29/610 R

[56] References Cited

U.S. PATENT DOCUMENTS

| | | | |
|---|---|---|---|
| 2,758,256 | 8/1956 | Eisler | 338/322 X |
| 3,314,033 | 4/1967 | Wnuk, Jr. | 338/25 X |
| 3,676,820 | 7/1972 | Taguchi | 338/34 |
| 4,167,725 | 9/1979 | Shimizu et al. | 422/98 X |
| 4,298,855 | 11/1981 | Mills | 338/35 |

*Primary Examiner*—C. L. Albritton
*Attorney, Agent, or Firm*—Ostrolenk, Faber, Gerb & Soffen

[57] ABSTRACT

A dew sensor comprising a substrate (1), a pair of detecting electrodes (2, 3) and a plurality of humidity sensitive members (4), the plurality of humidity sensitive members (4) connecting said opposing detecting electrodes (2, 3) on the substrate (1) and thus the detecting electrodes (2, 3) being at least in part exposed or uncovered.

6 Claims, 4 Drawing Figures ium complex oxide as a humidity sensitive member.
DEW SENSOR

BACKGROUND OF THE INVENTION

1. Field of the Invention

The present invention relates to a dew sensor, and more specifically to an improvement in the structure of a dew sensor.

2. Description of the Prior Art

Dew sensors having a resistance value which decreases with an increase of humidity (that is, dew sensors showing a negative humidity-resistance characteristic) are known. Examples of such dew sensors are dew sensors using a thick film in which conductive powder and dew sensors semiconductor powder is dispersed, or using ceramics which mainly contains titanium complex oxide as a humidity sensitive member.

Although detecting electrodes are generally used for detecting variations in resistance value, it is common to structure the humidity sensitive device such that the humidity sensitive member is formed to cover all of top surface of detecting electrodes. More specifically, the humidity sensitive member is formed to cover entirely a pair of electrodes, for example, a pair of parallel electrodes or a pair of comb-shaped electrodes, as detecting electrodes. U.S. Pat. No. 4,263,576, issued Apr. 21, 1981 discloses dew sensors as described above.

SUMMARY OF THE INVENTION

The inventors of the present invention discovered that a dew sensor, which is more sensitive than the conventional dew sensors described above, is obtained by structuring detecting electrodes to be at least in part exposed in the region in which the humidity sensitive member is formed.

Briefly, the present invention comprises a substrate, a pair of opposing detecting electrodes formed on the substrate, and a plurality of humidity sensitive members formed on the substrate, the plurality of humidity sensitive members connecting opposing detecting electrodes. Therefore, opposing detecting electrodes are at least in part exposed, that is, they are at least in part uncovered with the humidity sensitive members. As a result, the present inventive dew sensor is more sensitive than any of the conventional dew sensors. More particularly, the present inventive dew sensor can be advantageously applied to detecting devices utilizing ion conduction.

The humidity sensitive members of the present invention may be formed on the detecting electrodes, or the detecting electrodes may be formed on humidity sensitive members. The humidity sensitive member may be a humidity sensitive portion between opposing detecting electrodes, and thus a plurality of humidity sensitive members may be connected at their own end to each other. Furthermore, the humidity sensitive members may have a characteristic that its resistance value decreases with an increase in humidity.

Accordingly, it is an object of the present invention to provide a dew sensor being more sensitive than the conventional dew sensors.

Another object of the invention is to provide a dew sensor having a large variation range of the resistance value.

These objects and other objects, features, aspects, and advantages of the present invention will become more apparent from the following detailed description of the present invention when taken in conjunction with the accompanying drawings.

DESCRIPTION OF THE PREFERRED EMBODIMENTS

Figure 1:
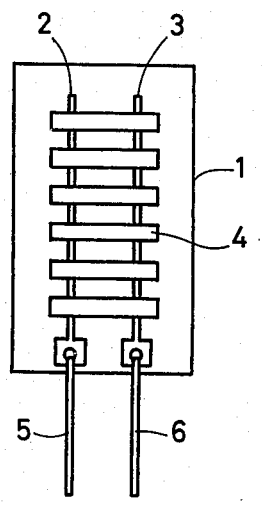
FIG. 1 is a plan view showing one embodiment of the invention.

FIG. 1 shows a plan view of a dew sensor in accordance with one embodiment of the invention. Numeral 1 denotes an insulating substrate made of insulating materials such as alumina, zirconia and the like, and numerals 2, 3 denote a pair of detecting electrodes, which are made of a parallel pair conductive members of for example gold. Numeral 4 denotes a humidity sensitive member formed on the detecting electrodes 2, 3, and a plurality of strips of the humidity sensitive members are formed to be spaced apart from each other so as to combine detecting electrodes 2, 3 with each other. Numerals 5, 6 denote lead wires, which are connected to the end portions of the detecting electrodes 2, 3 by soldering.

Figure 2:
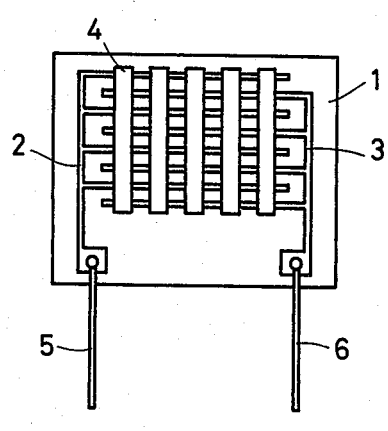
FIG. 2 is a plan view showing another embodiment of the invention.

FIG. 2 is a plan view showing a dew sensor of another embodiment in accordance with the invention. Although the dew sensor shown in FIG. 2 is substantially the same as the dew sensor shown in FIG. 1 in principal structure, the difference of the former from the latter is that detecting electrodes 2, 3 are made of a pair of comb-shaped conductive members. Other structures are substantially the same as the counterparts shown in FIG. 1, and thus a detailed description thereof is omitted.

Figure 3:
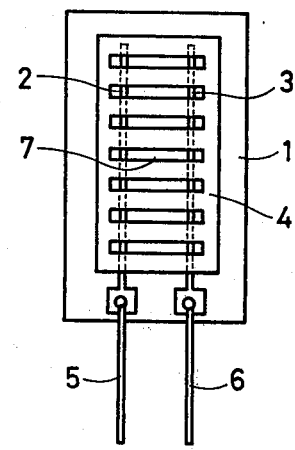
FIG. 3 is a plan view showing still another embodiment of the invention.

FIG. 3 is a plan view of a dew sensor of still another embodiment of the present invention. Referring to FIG. 3, although a plurality of humidity sensitive members 4 are formed to have a space therebetween in the same manner as the above described embodiments shown in FIGS. 1 and 2, the FIG. 3 embodiment is different from the FIGS. 1 and 2 embodiment in that both ends of the humidity sensitive members 4 are connected to each other. More particularly, the plurality of humidity sensitive members 4 may be formed from a single sheet in which a plurality of slits 7 are formed in the vertical direction to the detecting electrodes 2, 3. Other structures are substantially the same as the counterparts shown in FIGS. 1 and 2, and thus a detailed description thereof is omitted.

Figure 4:
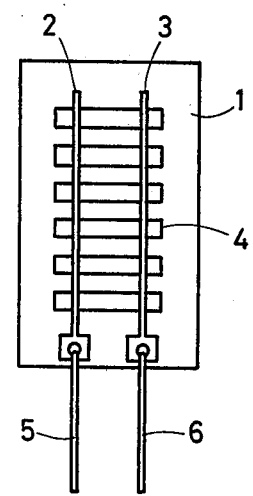
FIG. 4 is a plan view showing a further embodiment of the invention.

FIG. 4 is a plan view of a dew sensor of a further embodiment of the invention. Referring to FIG. 4, a plurality of strips of humidity sensitive member 4 are formed on an insulating substrate 1 and detecting electrodes 2, 3 are formed on the humidity sensitive members 4. The dew sensor of the FIG. 4 embodiment differs from the dew sensor shown in FIG. 1 in that the locations of the detecting electrodes 2, 3 and the humidity sensitive member 4 are reversed in the vertical direction. Of course, also in dew sensors shown in FIGS. 2 and 3, the detecting electrodes 2, 3 can be formed on the humidity sensitive members 4 as shown in FIG. 4.

In addition, it should be understood that the shape of detecting electrodes 2, 3 is not limited to them shown in figures. For example, it may be the helical shape. After all, the shape of detecting electrodes 2, 3 may have any shape so long as they can detect a resistance value variation of humidity sensitive members 4.

EXAMPLE

Now, the dew sensor in accordance with the invention will be explained based upon a specific example.

0.9 g of epoxy resin was admixed with 4.7 g of $MnO_2$ and 3.8 g of $TiO_2$. The same was further admixed with an alcohol solution of zirconium oxychoride, thereby to provide a paste as a humidity sensitive member.

On the other hand, the opposing detecting electrodes of gold were formed on an alumina substrate with the opposite distance of 0.5 mm and the opposite length of 66 mm. Then the above described paste was coated on the detecting electrodes. In the coating step, keeping the coating area of the paste to the humidity sensitive member constant, i.e. 55 mm$^2$, three samples were prepared by changing a coating pattern. Sample 1 was formed so that the detecting electrodes were entirely coated with the paste. Sample 2 was formed so that 10% of the top area of electrodes were exposed or uncoated, and sample 3 was formed so that 33% of the top area of electrodes were exposed or uncoated, and sample 4 was formed so that half of the top area of electrodes were exposed. Then all the samples were heated at the temperature of 150° C.

As to each sample, a response time and a resistance value were measured in the condition where dew was deposited on the sensor at the temperature of 25° C. and the relative humidity of 40% and the result is shown in the following table. Meanwhile, the initial resistance value of all the samples was $10^4$ M.

TABLE

| Sample No. | Required Time to Attain to 1 M (sec) | Resistance Value at Bedewed State (k) |
|---|---|---|
| Sample 1 | 100 | 1000 |
| Sample 2 | 80 | 800 |
| Sample 3 | 50 | 475 |
| Sample 4 | 30 | 310 |

As seen from the TABLE, samples 2, 3 and 4 show a shorter response time and a larger resistance value variation from the initial resistance value than the conventional dew sensor (sample 1). This is believed to be due to the fact that ion conduction readily occurs because of many boundary areas between the humidity sensitive members and the alumina substrate. Another reason is also believed to be that even if deposited dew or water is dissolved, gases which are produced facilitate the release of dew or water from the humidity sensitive members, and that it also facilitates ion conduction and increases the detecting sensitivity of the sensor. Furthermore, the inventive dew sensor has a characteristic in which the deposited water readily penetrates from gap portions to the humidity sensitive members as the humidity sensitive members are formed to have a space or gap therebetween and thus the inventive sensor is not subject to the the effect of contamination of the surface of the humidity sensitive members even if the surface of the humidity sensitive members are contaminated.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A dew sensor, comprising:
    a substrate,
    a pair of opposing detecting electrodes formed on said substrate, and
    a plurality of humidity sensitive members formed on said substrate, said plurality of humidity sensitive members being spaced apart and each connecting said opposing detecting electrodes such that a plurality of exposed boundary areas are formed between said humidity sensitive members and said electrodes.

2. A dew sensor in accordance with claim 1, wherein said humidity sensitive members are formed on said detecting electrodes.

3. A dew sensor in accordance with claim 1, wherein said detecting electrodes are formed on said humidity sensitive members.

4. A dew sensor in accordance with any one of claims 1, 2 or 3, wherein the resistance of said humidity sensitive members decreases with increasing humidity.

5. A dew sensor in accordance with claim 1, wherein a first end of each said humidity sensitive member is connected to a first end of each of the other said humidity sensitive members and a second end of each said humidity sensitive member is connected to the second end of each of the other said humidity sensitive members.

6. A dew sensor in accordance with claim 1, wherein said plurality of humidity sensitive members are not connected to each other.

* * * * *